United States Patent [19]
Arroyo et al.

[11] Patent Number: 5,147,366
[45] Date of Patent: Sep. 15, 1992

[54] PRESSURIZATION OF BONE CEMENT SURROUNDING AN ENDOPROSTHESIS

[75] Inventors: Nestor A. Arroyo, East Windsor; Casper F. Stark, Pompton Lakes; Raymond W. Augustin, Kendall Park, all of N.J.

[73] Assignee: Pfizer Hospital Products Group, Inc., New York, N.Y.

[21] Appl. No.: 487,342

[22] Filed: Mar. 1, 1990

[51] Int. Cl.$^5$ .............................................. A61B 17/56
[52] U.S. Cl. ........................................ 606/94; 606/92
[58] Field of Search ...................................... 606/92-94

[56] References Cited

U.S. PATENT DOCUMENTS

| | | | |
|---|---|---|---|
| 4,274,163 | 6/1981 | Malcom et al. | 623/18 |
| 4,357,716 | 11/1982 | Brown | 623/18 |
| 4,399,814 | 8/1983 | Pratt et al. | 128/92 VP |
| 4,462,394 | 7/1984 | Jacobs | 128/92 VP |
| 4,466,435 | 8/1984 | Murray | 128/92 VP |
| 4,488,549 | 12/1984 | Lee et al. | 128/303 |
| 4,562,598 | 1/1986 | Kranz | 623/18 |
| 4,595,006 | 6/1986 | Burke et al. | 128/303 |

FOREIGN PATENT DOCUMENTS 3835853  4/1990  Fed. Rep. of Germany ........ 606/95

*Primary Examiner*—Robert A. Hafer
*Assistant Examiner*—Kevin G. Rooney
*Attorney, Agent, or Firm*—Peter C. Richardson; Lawrence C. Akers; Raymond W. Augustin

[57] ABSTRACT

A method and apparatus for use in reducing the volatilization of the monomer component of bone cement is used after a prosthesis is implanted and throughout the polymerization of bone cement. The apparatus includes a generally annular inflatable sealing member having a centrally located opening therein for fitting over the exposed end of the prosthesis. The sealing member has an outer diameter covering the exposed surface of the bone cement. The sealing member has a deformable surface disposed in a substantially co-planar relationship with the exposed surface of the bone cement. The sealing member is resiliently expandable by inflation and extends beyond the edges of the bone defining the cavity, to seal the bone cavity upon the deformation of the deformable surface thereon. A pump is provided for inflating the sealing member and causing the deformable surface to apply pressure to the exposed surface of the bone cement. A valving system and a pressure gage are used for controlling the pressure applied to the exposed surface of the bone cement within a range of from 8-14 psi.

4 Claims, 2 Drawing Sheets

PRESSURIZATION OF BONE CEMENT SURROUNDING AN ENDOPROSTHESIS

FIELD OF THE INVENTION

This invention relates to a method and apparatus for pressurizing bone cement in situ, during polymerization. More particularly, the invention relates to a method and apparatus which can be utilized to pressurize the bone cement after a prosthesis is implanted in a medullary canal of the femur.

DESCRIPTION OF THE PRIOR ART

It is well known by laboratory experiments that the strength of curing polymethyl methacrylate (PMMA) bone cement is enhanced if the bone cement is put under pressure during polymerization. It is believed that this strength enhancement is the result of the reduced volatilization of the monomer component of the bone cement during polymerization. It is also well known that placing polymethyl methacrylate bone cement under pressure prior to the insertion of an implantable prosthesis improves the strength of the interlock between the cement and the bone into which the cement is placed. This is because the cement is thus encouraged to penetrate into the interstices of the cancellous bone structure. Clearly both of these effects are desirable.

A number of devices are available which attempt to carry out cement pressurization prior to the insertion of the prosthesis. One such device is referred to in U.S. Pat. No. 4,399,814 which issued to George W. Pratt, Jr. et al. and is used in a method of coating a portion of the walls of the medullary canal in effecting a degree of penetration into the bone with a coating of bone cement. The pressure on the bone cement is maintained until it reaches a desired physical state. However, this device does not allow the positioning of the prosthesis within the canal during the pressurization and also during polymerization, but only allows pressurization prior to insertion. Similarly, U.S. Pat. No. 4,488,549, which issued to Allen J. C. Lee, et al., refers to a method in which a pressurizable seal member fits over the end of the cavity in the bone to allow pressurization of the cement in the cavity. The seal member has an aperture therein for receiving a cement delivery nozzle. The seal member may be a balloon seal which is inflatable and expandable or a solid body of deformable material. Again, pressurization is accomplished prior to inserting the prosthesis. Therefore, the device is unsuitable for applying pressure to the bone cement during polymerization with the prosthesis in place.

U.S. Pat. No. 4,357,716, which issued to Byron L. Brown, refers to an apparatus which can seal the proximal end of the femur during total hip displacement after the bone cement has been placed around the prosthesis. While this patent provides a device which allows constant pressurization of the cement while the cement is hardening, there is no means of ensuring that optimum pressurization is occurring. Furthermore, the design of the device requires that the prosthesis have an integral collar so that mechanical forces can be applied and thereby compress the exposed surface of the bone cement. U.S. Pat. No. 4,274,163, which issued to Lawrence L. Malcom et al., refers to a prosthesis having internal passageways which allows for the introduction of bone cement under pressure. The pressure is maintained until the cement hardens.

U.S. Pat. Nos. 4,462,394, 4,466,435 and 4,595,006 disclose other methods for introducing bone cement into an intramedullary canal prior to the insertion of the prosthesis. U.S. Pat. No. 4,562,598, issued to C. Krang, refers to a pressing member for pressing a prepeg member into the walls of the bone cavity. None of these patents discloses a method or apparatus which can be used with a wide variety of existing prosthetic devices, nor do they allow for the maintenance of a predetermined pressure on the exposed surface of the bone cement during polymerization with the prosthesis implanted.

SUMMARY OF THE INVENTION

It is an object of the invention to provide a method and apparatus for pressurizing bone cement in an intramedullary canal after insertion of the prosthesis and while the bone cement is undergoing polymerization.

It is yet another object of the invention to provide a method and apparatus which indicates to the user the pressure being applied to the exposed surface of the bone cement during the polymerization process.

It is still another object of the invention to provide a method and apparatus for maintaining the pressure on the exposed surface of a bone cement during the polymerization thereof, with a prosthesis in place, which is simple in design and easy to operate.

Accordingly, these and other related objects are achieved by a preferred apparatus for use in applying a predetermined pressure to an exposed surface of a curable bone cement during the curing thereof. In this application, the bone cement surrounds an exposed end of a prosthesis implanted in a bone cavity. The preferred apparatus comprises an inflatable sealing member having a central opening therein for fitting over the exposed end of the prosthesis and covering the exposed surface of the bone cement. The sealing member has a deformable surface disposed in substantially co-planar relationship with the exposed surface of the bone cement and extends beyond the edges of a bone, defining the cavity to seal the bone cavity upon the deformation of the deformable surface.

The sealing member of the preferred apparatus comprises a flexible fluid-containing bladder having a bottom surface comprising the deformable surface. The preferred apparatus further includes a rigid body having a downwardly open recess formed in a bottom surface thereof for receiving the flexible fluid-containing bladder with the deformable surface disposed adjacent to the downward opening of the recess.

A pump is used for inflating the sealing member and enabling the deformable surface to apply pressure to the exposed surface of the cement. A pressure gage is used for controlling the pressure applied on the exposed surface of the bone cement, by the sealing member, to within a predetermined range.

The preferred bladder is resiliently expandable by inflation with the pump. The pump for inflating the flexible fluid-filled bladder includes a cylindrical fluid reservoir formed within the rigid body. A piston is operatively mounted within the cylindrical fluid reservoir and is moveable from a first position within the fluid reservoir to a second position during which movement fluid is expelled from the fluid reservoir. A conduit connecting the fluid reservoir to the flexible fluid-containing bladder is provided for conducting the fluid expelled by the piston to the inflatable bladder for the inflation thereof. A check valve is mounted in the conduit for preventing fluid from flowing back through the conduit from the fluid-containing bladder to the reservoir. A relief valve is provided for deflating the fluid-containing bladder by relieving the pressure therein.

A preferred method for reducing the volatilization of the monomer component of bone cement in a bone cavity during polymerization thereof comprises the step of inserting the prosthesis into the bone cavity. The prosthesis within the bone cavity is surrounded with bone cement prior to the completion of the polymerization thereof. Immediately after this filling operation, a predetermined pressure is applied to the exposed surface of bone cement surrounding the prosthesis. This predetermined pressure on the exposed surface of the bone cement is maintained until the polymerization is complete.

The preferred method further includes the step of sealing the bone cavity during the application of pressure, with the pressure being applied and maintained being 8–14 pounds per square inch (psi) of exposed bone cement. The preferred method uses a sealing member comprising a flexible fluid-filled bladder which is deformed by increasing the pressure of the fluid therein. The deformation of the flexible fluid-filled bladder is produced, at least in part, by pumping additional fluid into the bladder.

An alternate method for applying pressure to the exposed surface of the curable bone cement surrounding the exposed end of the prosthesis, implanted in the bone cavity during the curing of the cement, comprises the step of covering the exposed surface of the bone cement with a deformable sealing member. The sealing member is sized to extend beyond the edges of the bone defining the bone cavity. The sealing member is then deformed so as to apply pressure to the exposed surface of the bone cement and to seal the bone cavity. The pressure within said sealing member is then measured. A predetermined pressure is maintained on the exposed surface of the bone cement until curing is complete.

In this method, the sealing member can be a flexible fluid-filled bladder which is deformed by increasing the pressure of the fluid therein. This increase in pressure and the deformation of the flexible fluid-filled bladder is produced, at least in part, by pumping additional fluid into the bladder. The predetermined pressure is between 8–14 psi.

These and other objects are advantages of the present invention and will become apparent from the following description of the accompanying drawings, which disclose one embodiment of the invention. It is to be understood that the drawings are to be used for the purposes of illustration only and not as a definition of the invention.

BRIEF DESCRIPTION OF THE DRAWINGS

In the drawings wherein similar reference characters denotes similar elements throughout the several views.

DESCRIPTION OF THE PREFERRED EMBODIMENT

Figure 1:
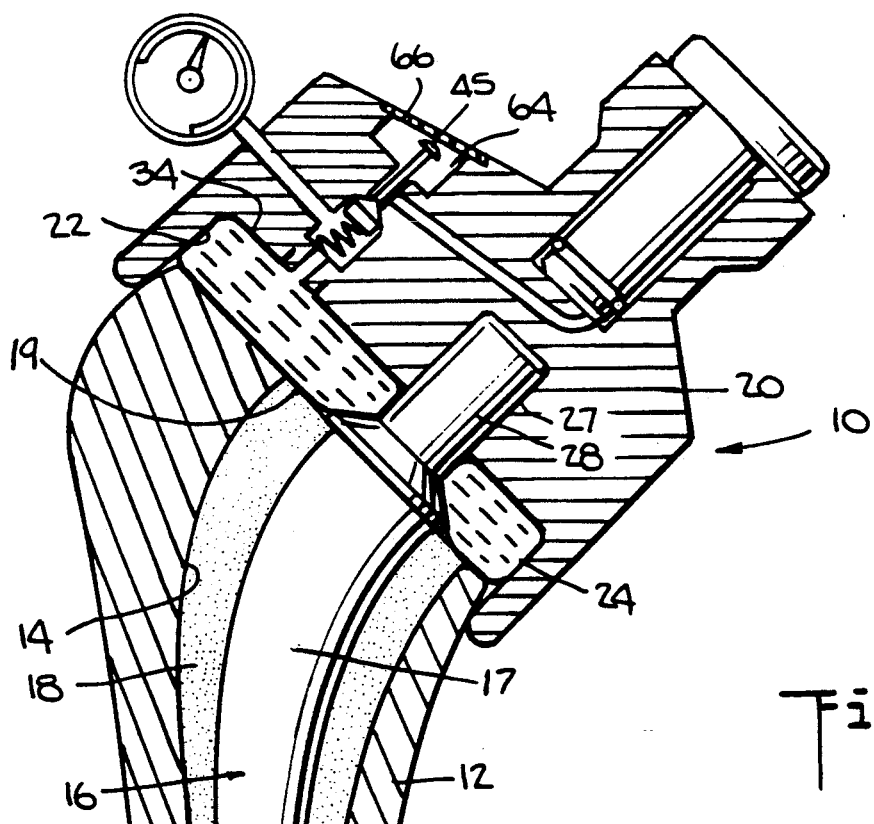
FIG. 1 is a cross-sectional side view of a femur including the apparatus of the present invention mounted at the proximal end thereof.

Referring to FIG. 1, there is shown the apparatus of the present invention, generally denoted as 10, mounted on the prepared proximal end of a femur 12. Femur 12 includes a prepared intramedullary canal 14 in which a femoral component 16 having a stem 17 has been inserted and has been surrounded by bone cement 18. The preferred bone cement is a two part polymethyl methacrylate system in which a liquid monomer and a powdered monomer component are mixed prior to being placed in intramedullary canal 14.

Apparatus 10 includes a rigid body 20 formed of metal or a suitable plastic. Rigid body 20 has a downwardly open recess 22 formed in a bottom surface 34 thereof. An annular shaped inflatable bladder 24 is housed within downwardly open recess 22. Deformable bladder 24 has an annular or donut shape and may be inflated with a suitable fluid such as a saline solution or other biocompatible liquid. The inner hole or opening 26 of inflatable bladder 24 is sized to fit over the trunion 28 of a wide variety of femoral components 16. Inflatable bladder 24 includes an inlet 30 having the form of a generally annular extension 31 which, in the preferred embodiment, is adapted to be sealingly received in a groove 33 surrounding an outlet 32 formed on the bottom surface 34 of rigid body 20.

Inlet 32 communicates with a passageway 36 leading to a valve system 38. Valve system 38 includes a check valve element 40 which is movable in a valve chamber 46. Element 40 is spring loaded to a closed position by spring 44. Spring 44 is mounted within chamber 46 at one and thereof. Chamber 46 communicates with inflatable bladder 24 via conduit 36 and inlet 32. A passageway 48 also communicates with chamber 46 through an outer wall of rigid body 20. A pressure gage is mounted so that pressure gage 50 can measure the pressure within the chamber 46 and therefore within inflatable bladder 24. A conduit 52 communicates with chamber 64 of valve element 40 opposite chamber 46 so that when valve element 40 is in the open position, conduit 52 may communicate with inflatable bladder 24 via chamber 46, conduit 36 and inlet 32.

Valve element 40 has a conically shaped surface 41 which engages a mating of conically shaped surface 47 at the end of chamber 46 opposite the end thereof where spring 44 is located. The cooperation between surfaces 47 and 41 serves to seal chamber 46 from conduit or passageway 52.

Conduit 52 in turn is connected to a pump element generally denoted as 54 which, in the preferred embodiment, is a piston cylinder arrangement. In this arrangement, a piston 56 is slidably mounted within a cylinder 58 for axial movement therein. An 0-ring 59 is provided to seal piston 56 as it moves axially within cylinder 58.

Figure 4:
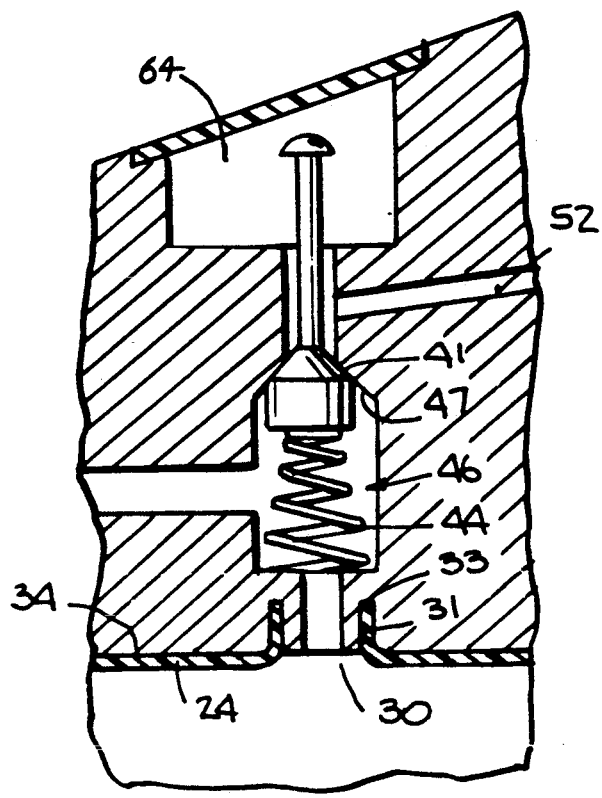
FIG. 4 is an enlarged cross-sectional view of the bladder attachment of the present invention.

Referring to FIG. 4, there is shown an enlarged cross sectional view of inflatable bladder 24 with inlet 30 thereof inserted within groove 33 of rigid body 20. Annular extension 31 of inlet 30 has a wall thickness sized such that there is an interference fit within the groove 33 formed in rigid body 20. Consequently, upon insertion of extension 31 in groove 33 a tight seal is formed, thereby preventing leakage of fluid within inflatable bladder 24 upon pressurization thereof.

A second chamber 64 is formed within rigid body 20 and contains upper end 45 of valve element 40. Chamber 64 is outwardly open with respect to rigid body 20 but is sealed with an elastomeric element 66. Elastomeric element 66 is preferably made of silicone rubber having a resiliency such that it may be deformed inwardly by applying pressure thereto, thus contacting end 45 of valve element 40 and moving valve element 40 against the biasing force of spring 44.

Figure 2:
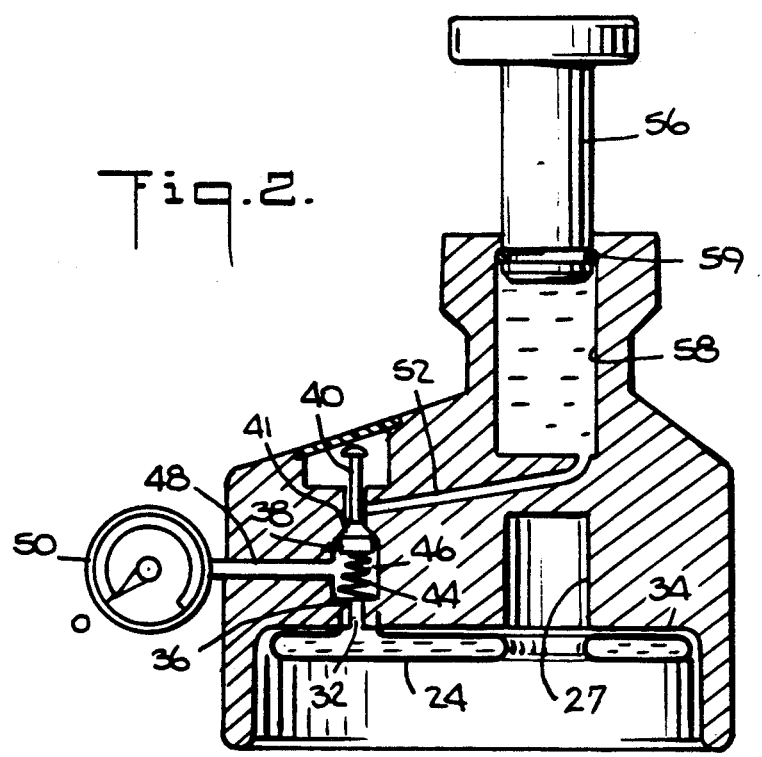
FIG. 2 is a cross-sectional side view of the apparatus of the present invention prior to pressurization.
Figure 5:
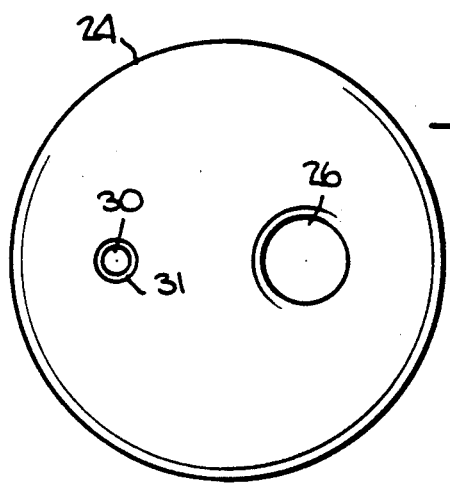
FIG. 5 is a plane view of the inflatable bladder of the present invention.
Figure 3:
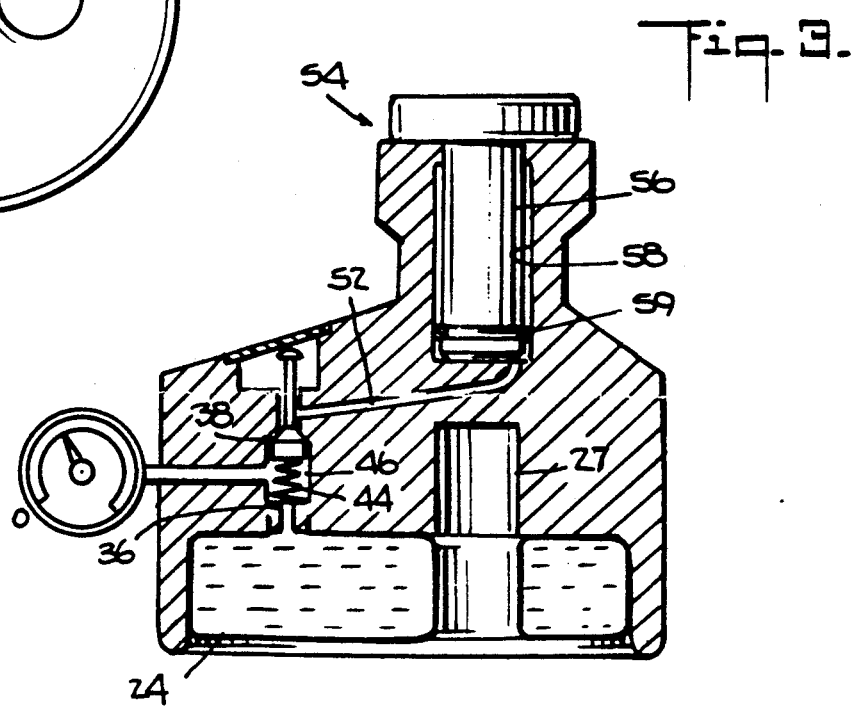
FIG. 3 is a cross-sectional side view of the apparatus of the present invention after inflation.

Referring to FIGS. 2 and 3, the preferred method of operation of the device of the present invention can be described. Initially, as shown in FIG. 2, piston 56 is in an extended position such that cylinder 58 is filled with the suitable fluid. Valve element 40 is in the upper position, and because of tapered surface 41 thereof and mating tapered surface 47 formed on chamber 46, a seal is created preventing fluid flow from conduit 52 to inflatable bladder 24. The surgeon would first mix the normally two component bone cement and fill the already prepared bone cavity with the cement 18. He would then insert femoral component 16 leaving trunion 28 thereof exposed. Rigid body 20 includes cavity 27, sized to snugly receive trunion 28.

Inflatable bladder 24 is mounted within recess 22 of apparatus 10 in manner so that hole 26 thereof is aligned with cavity 27 in body 20. Bladder 24 is so constructed that when hole 26 is so aligned, annular extension 31 is aligned with groove 33 in body 20 and can be inserted therein. Trunion 28 of femoral component 16 is then inserted through hole 26 into cavity 27 of body 20.

The surgeon then depresses piston 56 thereby forcing fluid through conduit 52 into chamber 64. As the pressure in chamber 64 increases, valve element 40 moves downwardly against the biasing action of spring 44, allowing fluid from cylinder 58 to flow through chamber 46, conduit 36, inlet 30 and into inflatable bladder 24, causing it to expand or inflate as shown in FIG. 3. Since recess 22 has a diameter greater than the intramedullary canal reamed by the surgeon, it effectively seals bone cavity 14. As bladder 24 inflates, hole 26 therein contracts and causes sealing around trunion 28 of femoral component 16. The surgeon continues to depress piston 56 until a pressure of between 8 and 14 pounds per square inch (psi) is shown on gage 50.

This pressure is the pressure within chamber 46 and inflatable bladder 24. It is also the pressure being exerted upon the cement surface 19 surrounding stem 17 of the femoral component 16. Upon attaining this predetermined pressure, the surgeon would cease depressing piston 56 of the cylinder 58 so that no additional fluid would flow through the conduit 52 and into inflatable bladder 24. Upon cessation of the downward force on piston 56, fluid forces would cause it to move outwardly in cylinder 58, thereby relieving the pressure in conduit 52 and chamber 46, allowing pressure forces and spring 44 to again move valve element 40 against inclined surface 47, thereby causing valve element 40 to act as a check valve. Should any leakage in the system occur, the surgeon would read gage 50 as falling, and when the lower limit of 8 p.s.i. was reached, he would again pressurize the system. This could be done by depressing piston 56 or by placing more pressure on partially inflated bladder 24 via physical pressure on body 20 itself such as by pressing the body 20 against the proximal end of femur 12.

Polymerization usually takes about 12 to 15 minutes after the initial mixing of the liquid monomer and powdered monomer components of the polymethyl methacrylate bone cement. Therefore, if the bone cement 18 were inserted within the bone cavity 14 approximately 6 minutes after mixing, the surgeon should maintain the predetermined pressure of 8 to 14 p.s.i. for an additional 6 to 9 minutes to ensure that polymerization is complete. Upon the expiration of this time period, valve element 40 may be moved downwardly against the biasing action of spring 44 by depressing elastomeric element 66, thereby disengaging the inclined surfaces forming the check valve. Fluid forces would then move piston 56 upwardly in cylinder 58, causing bladder 24 to at least partially deflate. The device would then be removed from the proximal end of the femur with the femoral component now cemented therein. By allowing polymerization to occur under pressure, a much stronger bond is developed between the bone, the bone cement 18 and the stem 17.

The apparatus of the present invention is made of materials which can withstand temperatures in excess of 212° F. (100° C.) so that it may be easily sterilized. Bag or bladder 24 may be made of silicon rubber so that it can be sterilized or may be made of any other material and discarded after each use. As can be seen, inflatable bladder 24 can be easily attached and detached from body 20. The sterile fluid in cylinder 58 can be replaced after each use or can be sterilized by the same process used to sterilize the entire apparatus.

While only one embodiment of the present invention has been described, it is obvious that many changes and modifications may be made thereto, without departing from the spirit and the scope of the invention.

We claim:

1. An apparatus for use in applying a predetermined pressure to an exposed surface of a curable bone cement in an area surrounding an exposed end of a prosthesis, during the curing of the cement to achieve fixation of the prosthesis, the apparatus comprising:

a generally annular inflatable resiliently expandable fluid-containing sealing member having a deformable bottom surface having an opening therein for fitting over the exposed end of the prosthesis, said sealing member having an outer diameter extending beyond the exposed surface of the bone cement, said sealing member having a deformable surface disposed in a substantially co-planar relationship with the exposed surface of the bone cement and extending beyond the edges of a bone defining the cavity to seal the bone cavity upon the deformation of said deformable surface;

a rigid body having a downwardly open recess formed in a bottom surface thereof for receiving said resiliently expandable fluid-containing sealing member with said deformable surface disposed adjacent to the downward opening of said open recess;

a fluid reservoir formed within said rigid body;

a piston operatively mounted within said fluid reservoir and moveable from a first position within said fluid reservoir to a second position, such that fluid is expelled from the fluid reservoir as said movement progresses;

a passageway formed within said rigid body for connecting said fluid reservoir to said resiliently expandable sealing member;

means mounted in said passageway for permitting fluid expelled from said reservoir to flow through said passageway from said reservoir to said resiliently expandable fluid-filled sealing member, but preventing fluid from flowing through said passageway from said resiliently expandable fluid-filled sealing member to said reservoir;

means for inflating said sealing member and causing said deformable surface to apply pressure to said exposed surface of said cement;

means for controlling the pressure applied to the exposed surface of the bone cement by said sealing member to within a predetermined range; and means for deflating said fluid-filled sealing member by relieving the pressure therein.

2. The apparatus as set forth in claim 1 wherein said means for deflating said fluid-filled sealing member and said means for permitting and preventing fluid flow is a valve mounted in said passageway.

3. The apparatus as set forth in claim 1 wherein said means for controlling the pressure on the exposed surface of the bone cement includes a pressure gage measuring the pressure within said sealing member.

4. The apparatus as set forth in claim 1 wherein said predetermined pressure is 8-14 psi.

* * * * *